US 9,055,883 B2

(12) United States Patent
Tgavalekos et al.

(10) Patent No.: US 9,055,883 B2
(45) Date of Patent: Jun. 16, 2015

(54) SURGICAL NAVIGATION SYSTEM WITH A TRACKABLE ULTRASOUND CATHETER

(75) Inventors: Nora T. Tgavalekos, Tewksbury, MA (US); Dun Alex Li, Salem, NH (US); Peter Traneus Anderson, Andover, MA (US); Jonathan David Schiff, Andover, MA (US)

(73) Assignee: General Electric Company, Schenectady, NY (US)

( * ) Notice: Subject to any disclaimer, the term of this patent is extended or adjusted under 35 U.S.C. 154(b) by 1217 days.

(21) Appl. No.: 11/935,479

(22) Filed: Nov. 6, 2007

(65) Prior Publication Data

US 2008/0287860 A1 Nov. 20, 2008

Related U.S. Application Data

(60) Provisional application No. 60/938,434, filed on May 16, 2007.

(51) Int. Cl.

| | |
|---|---|
| *A61M 25/095* | (2006.01) |
| *A61B 5/06* | (2006.01) |
| *A61B 8/12* | (2006.01) |
| *A61B 8/00* | (2006.01) |
| *A61B 8/08* | (2006.01) |

(Continued)

(52) U.S. Cl.
CPC ............... *A61B 5/06* (2013.01); *A61B 5/0402* (2013.01); *A61B 5/0816* (2013.01); *A61B 8/12* (2013.01); *A61B 8/4245* (2013.01); *A61B 8/4461* (2013.01); *A61B 8/5238* (2013.01); *A61B 8/445* (2013.01)

(58) Field of Classification Search
CPC ...... A61B 5/0402; A61B 5/0816; A61B 5/06; A61B 8/445; A61B 8/5238; A61B 8/12; A61B 8/4245; A61B 8/4461; A61M 25/095
USPC .......................................... 600/466, 424, 463
See application file for complete search history.

(56) References Cited

U.S. PATENT DOCUMENTS

| 5,377,678 A | 1/1995 | Dumoulin et al. |
| 5,628,478 A * | 5/1997 | McConnel et al. ........... 246/194 |

(Continued)

FOREIGN PATENT DOCUMENTS

EP 1057455 A2 12/2000

OTHER PUBLICATIONS

Proulx, T.L. et al, "Advances in Catheter-Based Ultrasound Imaging", IEEE International Ultrasonics Symposium Proceedings, 2005.

(Continued)

*Primary Examiner* — Vani Gupta
(74) *Attorney, Agent, or Firm* — Andrus Intellectual Property Law, LLP

(57) ABSTRACT

A surgical navigation system including an ultrasound catheter is disclosed herein. The ultrasound catheter includes a flexible catheter housing defining a distal end, a transducer array disposed at least partially within the catheter housing, and a motor coupled with the transducer array. The motor is configured to rotate the transducer array in order to image a three-dimensional volume. The ultrasound catheter also includes a tracking element adapted to provide an estimate of a position and/or orientation of the distal end of the catheter housing. The tracking element is disposed within the catheter housing and immediately adjacent to the distal end.

16 Claims, 3 Drawing Sheets

(51) Int. Cl.
*A61B 5/0402* (2006.01)
*A61B 5/08* (2006.01)

(56) References Cited

U.S. PATENT DOCUMENTS

| | | | |
|---|---|---|---|
| 5,630,417 A * | 5/1997 | Petersen et al. | 600/443 |
| 6,073,043 A | 6/2000 | Schneider | |
| 6,201,387 B1 * | 3/2001 | Govari | 324/207.17 |
| 6,233,476 B1 | 5/2001 | Strommer et al. | |
| 6,253,770 B1 * | 7/2001 | Acker et al. | 128/899 |
| 6,615,155 B2 | 9/2003 | Gilboa | |
| 6,669,635 B2 | 12/2003 | Kessman et al. | |
| 6,716,166 B2 | 4/2004 | Govari | |
| 6,773,402 B2 | 8/2004 | Govari et al. | |
| 7,090,639 B2 | 8/2006 | Govari | |
| 7,156,816 B2 | 1/2007 | Schwartz et al. | |
| 7,158,754 B2 | 1/2007 | Anderson | |
| 2001/0031919 A1 | 10/2001 | Strommer et al. | |
| 2002/0005719 A1 | 1/2002 | Gilboa et al. | |
| 2002/0026118 A1 | 2/2002 | Govari | |
| 2002/0042571 A1 | 4/2002 | Gilboa et al. | |
| 2003/0013958 A1 | 1/2003 | Govari et al. | |
| 2003/0074011 A1 | 4/2003 | Gilboa et al. | |
| 2003/0088179 A1 * | 5/2003 | Seeley et al. | 600/424 |
| 2003/0208102 A1 | 11/2003 | Gilboa | |
| 2003/0231789 A1 | 12/2003 | Willis et al. | |
| 2004/0097805 A1 | 5/2004 | Verard et al. | |
| 2004/0102769 A1 | 5/2004 | Schwartz et al. | |
| 2004/0114146 A1 * | 6/2004 | Willis | 356/446 |
| 2004/0138548 A1 | 7/2004 | Strommer et al. | |
| 2004/0162507 A1 | 8/2004 | Govari | |
| 2004/0162550 A1 | 8/2004 | Govari et al. | |
| 2004/0254458 A1 | 12/2004 | Govari | |
| 2005/0197557 A1 | 9/2005 | Strommer et al. | |
| 2006/0241445 A1 | 10/2006 | Altmann et al. | |
| 2006/0253024 A1 | 11/2006 | Altmann et al. | |
| 2006/0253029 A1 | 11/2006 | Altmann et al. | |
| 2006/0253030 A1 | 11/2006 | Altmann et al. | |
| 2006/0253031 A1 | 11/2006 | Altmann et al. | |
| 2006/0253032 A1 | 11/2006 | Altmann et al. | |
| 2007/0038110 A1 * | 2/2007 | Flesch et al. | 600/459 |
| 2007/0073135 A1 | 3/2007 | Lee et al. | |
| 2007/0078334 A1 * | 4/2007 | Scully et al. | 600/424 |
| 2007/0106147 A1 | 5/2007 | Altmann et al. | |
| 2007/0167801 A1 | 7/2007 | Webler et al. | |
| 2007/0167821 A1 | 7/2007 | Lee et al. | |
| 2007/0167827 A1 * | 7/2007 | Masters | 600/463 |
| 2007/0225593 A1 | 9/2007 | Porath et al. | |

OTHER PUBLICATIONS

Martin, R. et al, "A Miniature Position and Orientation Locator for Three Dimensional Echocardiography", IEEE Proceedings on Computer in Cardiology, pp. 25-28, 1993.
Beasley, R.A. et al, "Registration of ultrasound images", www.tgt.vanderbilt.edu/archive/Registration of ultrasound images.pdf, publication date: 1999.
Rotger, D. et al, "Multimodal Registration of Intravascular Ultrasound Images and Angiography", Computer Vision Center Universitat Autonoma de Barcelona Bellaterra, Spain, www.cvc.uab.es/~petia/caseib2002.pdf, publication date: 2002.
Huang, X. et al, "Dynamic 3D Ultrasound and MR Image Registration of the Beating Heart", MICAI, LNCS 3750, pp. 171-178, 2005.
Leotta, D.F. et al., "Three-Dimensional Ultrasound Imaging Using Multiple Magnetic Tracking Systems and Miniature Magnetic Sensors", IEEE on Ultrasonics Symposium, pp. 1415-1418, 1995.
Pagoulatos, N. et al., "Interactive 3-D Registration of Ultrasound and Magnetic Resonance Images Based on a Magnetic Position Sensor", IEEE on Info. Tech. In Biomedicine, vol. 3, No. 4, 1999.
USPTO Office Action mailed Sep. 13, 2010—U.S. Appl. No. 11/863,656, filed Sep. 28, 2007.
USPTO Office Action mailed Jul. 21, 2010—U.S. Appl. No. 11/866,865, filed Oct. 3, 2007.

* cited by examiner

SURGICAL NAVIGATION SYSTEM WITH A TRACKABLE ULTRASOUND CATHETER

RELATED APPLICATIONS

This application claims priority to Provisional Application No. 60/938,434 filed on May 16, 2007, and is hereby incorporated herein by reference in its entirety.

BACKGROUND OF THE INVENTION

The subject matter disclosed herein relates to a surgical navigation system operable to track an ultrasound catheter.

Surgical navigation systems implementing electro magnetic (EM) technology can track the position and/or orientation of a medical instrument and convey this location to a user. The position and orientation information can be conveyed by virtually superimposing a graphic representation of the distal end of the medical device onto a patient image. Accordingly, the user receives visual feedback to help navigate or guide the medical device to a target site.

Conventional surgical navigation systems generally include a tracking element disposed near the proximal end of the tracked instrument such that the tracking element does not interfere with the performance of the medical procedure. The tracking element may comprise a magnetic field generator or a magnetic field sensor, and may comprise one or more coils defining a variety of different coil configurations. As medical personnel are frequently more concerned with the position and orientation of the distal end of the medical instrument, it is often necessary to estimate the distance between a tracking element disposed near the proximal end of an instrument and the instrument's distal tip. One problem associated with tracking a catheter-based medical instrument is that catheters are flexible which may cause the distance between the proximal end and the distal end to vary. Another problem associated with tracking an ultrasound catheter device is related to interference from the ultrasound motor that can render any tracking system position and orientation estimates less precise.

BRIEF DESCRIPTION OF THE INVENTION

The above-mentioned shortcomings, disadvantages and problems are addressed herein which will be understood by reading and understanding the following specification.

In an embodiment, an ultrasound catheter includes a flexible catheter housing defining a distal end, a transducer array disposed at least partially within the catheter housing, and a motor coupled with the transducer array. The motor is configured to rotate the transducer array in order to image a three-dimensional volume. The ultrasound catheter also includes a tracking element adapted to estimate a position and/or orientation of the distal end of the catheter housing. The tracking element is disposed within the catheter housing and immediately adjacent to the distal end.

In another embodiment, a surgical navigation system includes an ultrasound catheter comprising a flexible catheter housing defining a distal end; a transducer array disposed at least partially within the catheter housing; and a motor coupled with the transducer array. The motor is configured to rotate the transducer array in order to image a three-dimensional volume. The surgical navigation system also includes a first tracking element adapted to provide an estimate of a position and/or orientation of the distal end of the catheter housing. The first tracking element is disposed near the distal end of the catheter housing so that the catheter housing flex does not appreciably diminish the precision of the position and/or orientation estimate. The surgical navigation system also includes a second tracking element disposed near the motor. The second tracking element is configured to record a noise signal produced by the motor.

In another embodiment, a surgical navigation system includes an ultrasound catheter comprising a flexible catheter housing defining a distal end, a transducer array disposed at least partially within the catheter housing, and a motor coupled with the transducer array. The motor is configured to rotate the transducer array in order to image a three-dimensional volume. The surgical navigation system also includes a first tracking element adapted to provide an estimate of a position and/or orientation of the distal end of the catheter housing. The first tracking element is disposed immediately adjacent to the distal end of the catheter housing so that catheter housing flex does not appreciably diminish the precision of the position and/or orientation estimate. The surgical navigation system also includes a second tracking element disposed near the motor. The second tracking element is configured to record a noise signal produced by the motor. The surgical navigation system also includes a tracking system connected to the first tracking element and the second tracking element. The tracking system is configured to compensate for the recorded noise signal from the second tracking element in a manner adapted to improve the precision of the position and/or orientation estimate from the first tracking element.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
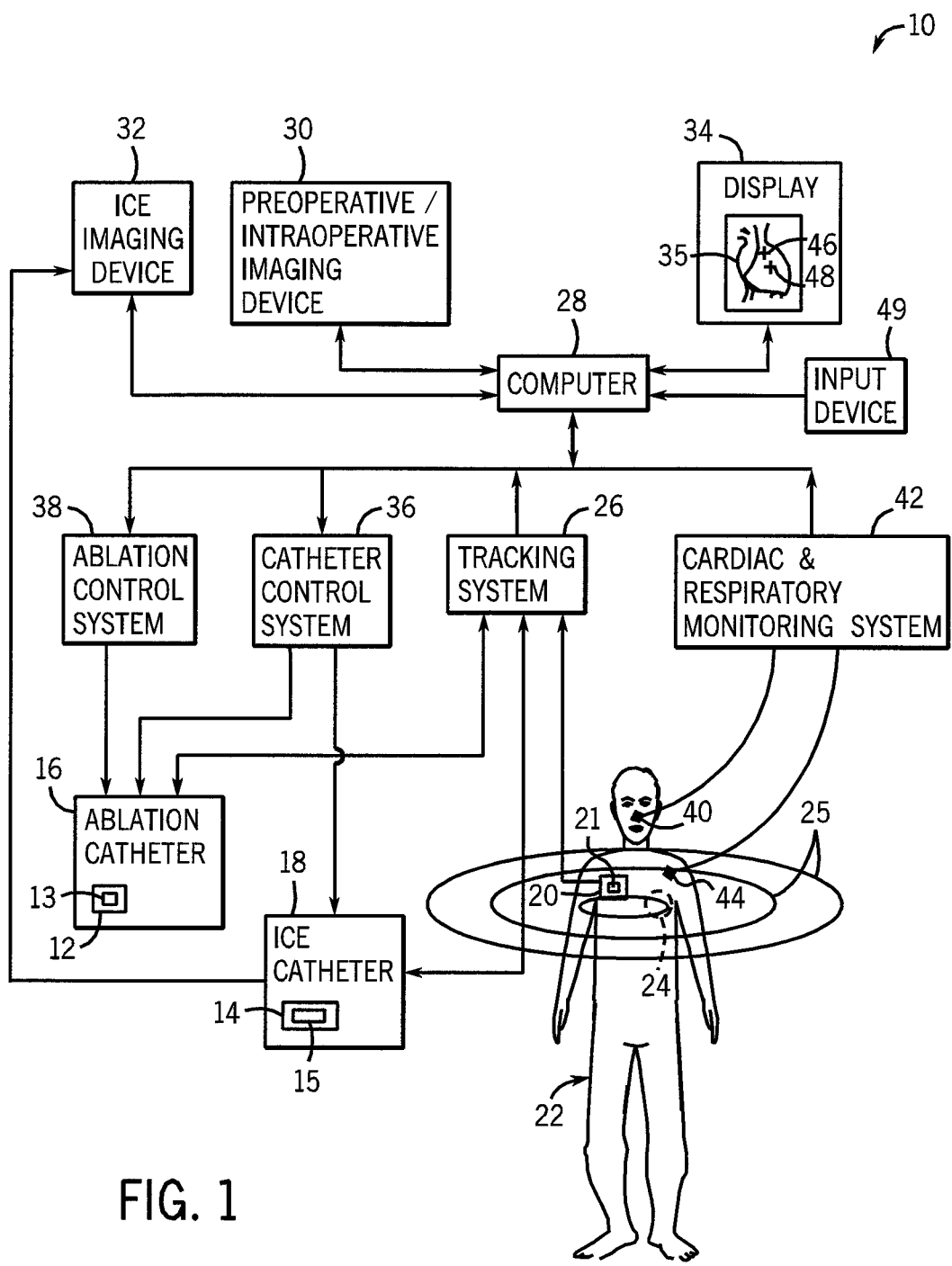
FIG. 1 is a schematic representation of an imaging and navigation system in accordance with an embodiment.

Referring to FIG. 1, a system 10 is shown in accordance with one embodiment. The system 10 will hereinafter be described as an imaging and navigation system adapted for treating atrial fibrillation using an ablation procedure. The system 10 will also hereinafter be described as implementing intra-cardiac echocardiography (ICE) to facilitate the performance of the ablation procedure. It should, however, be appreciated that the system 10 may also be implemented to treat other medical conditions and to perform other procedures, and that the system 10 may implement alternate ultrasonic technologies in place of ICE.

The navigation portion of the imaging and navigation system 10 includes a tracking system 26 that is operatively connected to a plurality of tracking elements 12, 14 and 20. The tracking element 12 is adapted for attachment to an ablation catheter 16, and the tracking element 14 is adapted for attachment to an ICE catheter 18. For purposes of this disclosure, a catheter is defined to include any flexible medical delivery system such as, for example, an endoscope. The tracking element 20 can be rigidly attached to an internal organ (e.g., the heart 24) or to the external body of the patient 22 in a conventional manner. A tracking element 20 secured to the patient's heart 24 may be referred to as a "dynamic reference" because it is adapted to move along with the heart 24. An exemplary method of attaching the tracking element 20 to the patient's heart 24 is through a minimally invasive procedure using a dynamic reference catheter (not shown).

The present invention will hereinafter be described in accordance with an embodiment wherein the tracking element 20 comprises a field generator 21, the tracking element 12 comprises a field sensor 13, and the tracking element 14 comprises a field sensor 15. It should, however, be appreciated that according to alternate embodiments the tracking element 20 may include a field sensor and the tracking elements 12, 14 may include field generators. The field generator 21 generates a magnetic field 25 in an area that includes the target site (e.g., the patient's heart 24). The field sensors 13, 15 are adapted to measure the magnetic field 25, and to transmit the magnetic field measurements to the tracking system 26. The tracking system 26 and/or the computer 28 implement the magnetic field measurements to calculate the position and orientation of the tracking elements 12, 14.

After calculating the position and orientation of the tracking elements 12, 14, the position and orientation of the ablation catheter 16 and the ICE catheter 18 respectively attached thereto can also be calculated in a known manner. According to one embodiment, the physical distance between the tracking elements 12, 14 and the distal end portions of the respective catheters 16, 18 are calculated and a translation/rotation matrix is applied as a conversion factor to the raw data from the tracking system 26. In this manner, an operator can track with a high degree of precision both the position and orientation of the distal end portions of the catheters 16, 18.

The computer 28 registers the position and orientation data to an image obtained from a preoperative/intraoperative imaging device 30 and/or to an image obtained from an ICE imaging device 32. The preoperative/intraoperative imaging system 30 may, for example, include a CT imaging device, a MR imaging device, a PET imaging device, an ultrasound imaging device, an X-ray imaging device, or any other known imaging device, as well as any combinations thereof. The preoperative/intraoperative imaging device 30 may provide 2D, 3D or 4D images. For purposes of this disclosure, 4D refers to the three primary dimensions (i.e., as measured along X, Y and Z axes) and the fourth dimension which is time. Therefore, for purposes of this disclosure, 4D is synonymous with generally real time 3D. Also for purposes of this disclosure, a generally real time image includes a maximum image delay of approximately one second. The ICE imaging device 32 is configured to obtain imaging data from the ICE catheter 18 and produce 2D, 3D or 4D images as will be described in detail hereinafter.

The catheter position and orientation data can be visualized on the display 34. According to one embodiment, graphic representations corresponding to the ablation catheter 16 and the ICE catheter 18 may be virtually superimposed on a patient image 35. In the embodiment of FIG. 1, the graphic representations corresponding to the catheters 16, 18 include the cross-hairs 46, 48 respectively representing the distal end portions of the ablation catheter 16 and the ICE catheter 18, however other embodiments may include a more complete rendering showing the catheters 16, 18 in detail. In a non-limiting manner, the patient image 35 may include a CT image, a MR image, a PET image, an ultrasound image or an X-ray image from the preoperative/intraoperative imaging device 30. The patient image 35 may also include a real time 3D image from the ICE imaging device 32, or a fused image comprising a plurality of images from the preoperative/intraoperative imaging device 30 and/or the ICE imaging device 32 that have been combined in a known manner.

The input device 49 may include any known apparatus or system such as a keyboard, mouse, touch screen, joystick, etc., and is generally adapted to allow a user to manually input data into the system 10. Although shown in FIG. 1 as a separate component, the input device 49 may alternatively be incorporated into one of the other system 10 components such as the computer 28 or the display 34. As an example, the input device 49 may include a touch screen device integrated into the design of the display 34 and adapted to facilitate surgical planning. According to one embodiment, the exemplary touch screen input device 49 could be implemented to highlight or otherwise identify specific regions of interest on a patient image obtained from one of the imaging devices 30, 32. According to another embodiment, the exemplary touch screen input device 49 could be implemented to assign a priority sequence to a plurality of regions of interest.

A catheter control system 36 is operatively connected to both the ablation catheter 16 and the ICE catheter 18. The catheter control system 36 is adapted to translate and steer the catheters 16, 18 through the patient 22 to a predefined destination at or near the patient's heart 24. The catheter control system 36 may be configured to translate and steer the catheters 16, 18 in response to manual operator inputs, or may be configured to automatically direct the catheters 16, 18 to a selectable target site. The catheter control system 36 may also be operatively connected to and configured to control a dynamic reference catheter (not shown) adapted to facilitate the attachment of the tracking element 20 to the patient's heart 24.

An ablation control system 38 controls the energy transfer to the ablation catheter 16. Accordingly, when an operator determines that the distal end of the ablation catheter 16 is in sufficiently close proximity to a targeted cardiac region, the ablation control system 38 can be implemented to transmit a selectable amount of energy. The transmission of energy in this manner kills or otherwise renders inactive the targeted region in order to break electrical pathways causing atrial fibrillation. In a non-limiting manner, the ablation control system 38 may implement radio frequency (RF), cryogenic, ultrasound, or laser technologies.

One or more respiratory sensors 40 can be positioned near the patient's mouth and/or nose in order to monitor respiration, and one or more cardiac sensors 44 can be positioned near the patient's heart 24 to monitor cardiac activity. The respiratory sensors 40 and the cardiac sensors 44 are operatively associated with and adapted to transmit sensor data to a monitoring system 42. Any sensor data collected by the monitoring system 42 is transferable to the computer 28 such that the computer 28 may be implemented to synchronize the operation of the tracking system 26, the imaging device 30, and/or the imaging device 32 with the patient's cardiac and respiratory activity. According to one example, the computer 28 may implement data from the monitoring system 42 to acquire images during predefined portions of a patient's cardiac or respiratory cycle. According to another example, the computer 28 may implement data from the monitoring system 42 to sequence a series of 2D images or slices in a manner that corresponds with a patient's cardiac or respiratory cycle in order to provide a generally real time rendering of a dynamic object such as the patient's heart 24.

Figure 2:
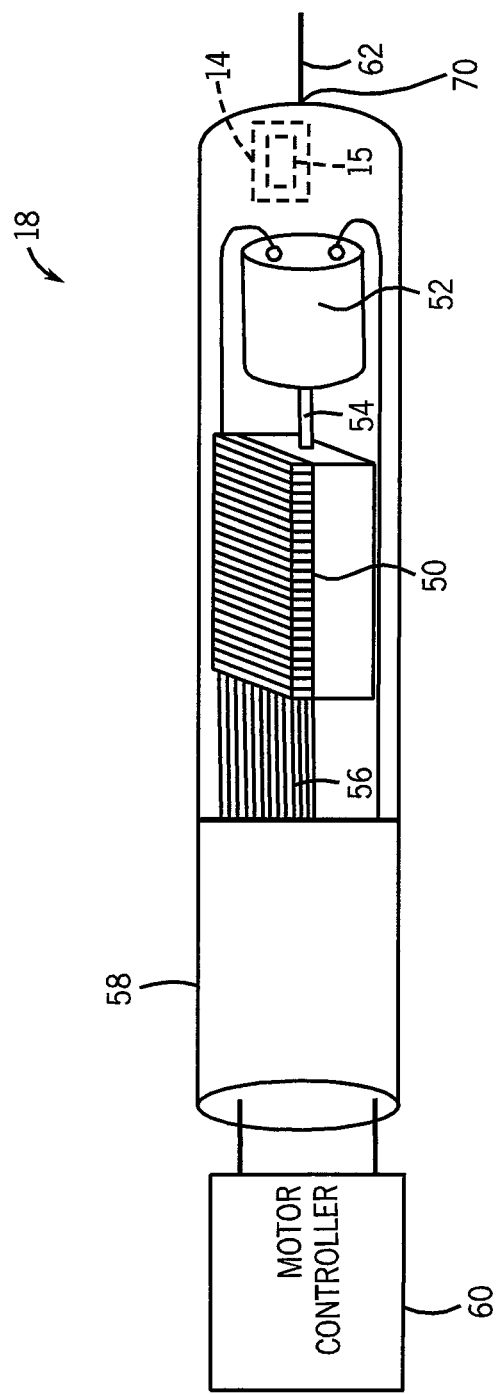
FIG. 2 is a partially cutaway schematic illustration of an ICE catheter in accordance with an embodiment.

Referring to FIG. 2, a more detailed illustration of the ICE catheter 18 is shown in accordance with one embodiment. It should be appreciated that the ICE catheter 18 is described for illustrative purposes, and that any catheter system adapted to retain an ultrasonic imaging device may alternatively be implemented in place of the ICE catheter 18.

The ICE catheter 18 comprises a transducer array 50, a motor 52, which may be internal or external to the space-critical environment, a drive shaft 54 or other mechanical connections between motor 52 and the transducer array 50, and an interconnect 56. The ICE catheter 18 further includes a catheter housing 58 enclosing the transducer array 50, motor 52, interconnect 56 and drive shaft 54. In the depicted embodiment, the transducer array 50 is mounted on drive shaft 54 and the transducer array 50 is rotatable with the drive shaft 54. The rotational motion of the transducer array 50 is controlled by motor controller 60 and motor 52. Interconnect 56 refers to, for example, cables and other connections coupling the transducer array 50 with the ICE imaging device 32 (shown in FIG. 1) for use in receiving and/or transmitting signals. In an embodiment, interconnect 56 is configured to reduce its respective torque load on the transducer array 50 and motor 52. The catheter housing 58 is of a material, size and shape adaptable for internal imaging applications and insertion into regions of interest. According to the embodiment depicted in FIG. 2, the catheter housing 58 is generally cylindrical defining a longitudinal axis 62.

The catheter housing 58, or at least the portion that intersects the ultrasound imaging volume, is acoustically transparent, e.g. low attenuation and scattering, acoustic impedance near that of blood and tissue (Z~1.5 M Rayl). The space between the transducer and the housing can be filled with an acoustic coupling fluid (not shown), e.g., water, with acoustic impedance and sound velocity near those of blood and tissue (Z~1.5 M Rayl, V~1540 m/sec).

According to one embodiment, the transducer array 50 is a 64-element one-dimensional array having 0.110 mm azimuth pitch, 2.5 mm elevation and 6.5 MHz center frequency. The elements of the transducer array 50 are electronically phased in order to acquire a sector image parallel to the longitudinal axis 62 of the catheter housing 58. The transducer array 50 is mechanically rotated about the longitudinal axis 62 to image a three-dimensional volume. The transducer array 50 captures a plurality of two-dimensional images as it is being rotated. The plurality of two-dimensional images are transmitted to the ICE imaging device 32 (shown in FIG. 1) which is configured to sequentially assemble the two-dimensional images in order to produce a three-dimensional image.

The rate at which the transducer array 50 is rotated about the longitudinal axis 62 can be regulated by the motor controller 60. The transducer array 50 can be rotated relatively slowly to produce a 3D image, or relatively quickly to produce a generally real time 3D image (i.e., a 4D image). The motor controller 60 is also operable to vary the direction of rotation to produce an oscillatory transducer array motion. In this manner, the range of motion and imaged volume are restricted such that the transducer array 50 can focus on imaging a specific region and can update the 3D image of that region more frequently, thereby providing a real-time 3D, or 4D, image.

Referring to FIGS. 1 and 2, the ICE catheter 18 includes an integrally attached tracking element 14 disposed within the catheter housing 58. The integrally attached tracking element 14 is adapted to work in combination with the tracking element 20 and the tracking system 26 to estimate the position and/or orientation of the ICE catheter 18. While the tracking element 14 is depicted as comprising the field sensor 15 in accordance with one embodiment, it should be appreciated that the tracking element 14 may alternatively comprise a field generator (not shown) similar to the field generator 21.

The field sensor 15 may comprise two or more coils adapted to track the ICE catheter 18 with six degrees of freedom. For purposes of this disclosure, the six degrees of freedom refer to the position along each of the three primary X, Y and Z axes as well as orientation or degree of rotation about each of the three primary axes (i.e., yaw, pitch and roll). The filed sensor 15 may define a variety of different coil configurations. According to one embodiment, the field sensor 15 comprises two generally co-located micro-coils. According to another embodiment, the field sensor 15 comprises three generally orthogonal coils defining an industry-standard-coil-architecture (ISCA) type configuration.

The tracking element 14 is positioned immediately adjacent to the distal end 70 of the catheter housing 58. For purposes of this disclosure, the term "immediately adjacent" refers to the depicted arrangement wherein there are no other components disposed between the tracking element 14 and the distal end 70.

As previously indicated, the system 10 may estimate the physical distance between the tracking element 14 and the distal end 70 of the catheter housing 58, and implement this estimate as a conversion factor to the raw data from the tracking system 26 in order to track the position and orientation of the distal end 70. The process of estimating the physical distance between the tracking element 14 and the distal end 70 of the catheter housing 58 is complicated by the fact that the catheter housing 58 is flexible thereby potentially causing the estimated distance to vary. By positioning the tracking element 14 near the distal end 70 of the catheter housing 58, the distance between the tracking element 14 and the distal end 70 remains generally constant regardless of catheter housing 58 flex. Accordingly, the precision with which the tracking system 26 estimates the position and orientation of the distal end 70 of the ICE catheter 18 is improved.

Figure 3:
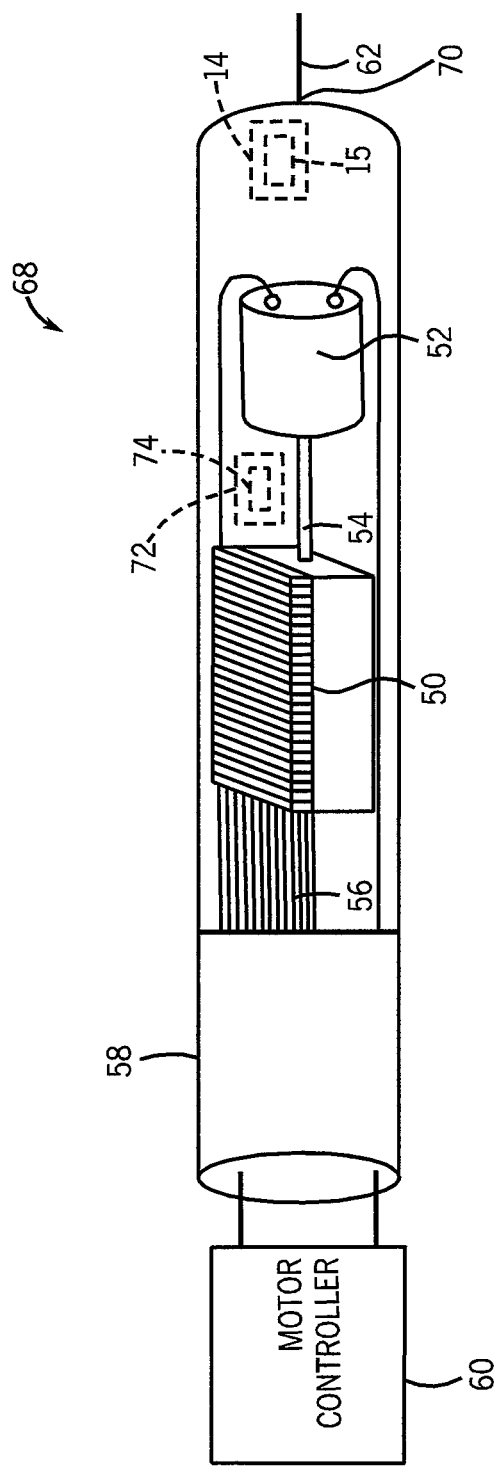
FIG. 3 is a partially cutaway schematic illustration of an ICE catheter in accordance with another embodiment.

Referring to FIG. 3, an ICE catheter 68 is shown in accordance with an embodiment. Common reference numbers are implemented to identify ICE catheter 68 elements that are generally identical to those of the ICE catheter 18 (shown in FIG. 2). It should be appreciated that the ICE catheter 68 is described for illustrative purposes, and that any catheter system adapted to retain an ultrasonic imaging device may alternatively be implemented in place of the ICE catheter 68.

The ICE catheter 68 includes all the components and features previously described with respect to the ICE catheter 18 (shown in FIG. 2), and additionally includes a tracking element 72. The tracking element 72 will hereinafter be described as comprising a field sensor 74 in accordance with one embodiment, however it should be appreciated that the tracking element 72 may alternatively comprise a field generator (not shown) similar to the field generator 21 (shown in FIG. 1). The field sensor 74 may comprise one or more coils defining a variety of different coil configurations. According to one embodiment, the field sensor 74 comprises three generally orthogonal coils defining an ISCA type configuration.

According to the depicted embodiment, the tracking element 72 is disposed within the catheter housing 58, and is positioned behind and in close proximity to the motor 52. According to another embodiment that is not shown, the tracking element 72 may be positioned in front of and in close proximity to the motor 52. By positioning the tracking element 72 in close proximity to the motor 52, the tracking element 72 can be implemented to track and record the noise signal attributable to motor 52 interference. By tracking and recording the noise signal attributable to motor 52 interference, the noise signal can be removed or otherwise accounted for in a known manner such that tracking system precision is improved. According to one embodiment, the tracking system 26 is configured to receive the recorded noise signal from the tracking element 72, and to compensate for the noise signal in a manner adapted to provide position and/or orientation estimates that are not predicated on noise signal data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An ultrasound catheter comprising:
   a flexible catheter housing defining a proximal end and a distal tip;
   a transducer array disposed at least partially within the flexible catheter housing;
   a motor positioned in the flexible catheter housing and coupled with the transducer array, said motor being configured to rotate the transducer array in order to image a three-dimensional volume;
   a first tracking element adapted to provide an estimate of a position and/or orientation of the distal tip of the flexible catheter housing, said first tracking element confined to the distal tip of the flexible catheter housing and immediately adjacent to the distal tip such that there are no other components disposed between the first tracking element and the distal tip so as to track the position and/or orientation of the distal tip with a high degree of precision despite catheter flex; and
   a second tracking element disposed within the flexible catheter housing in close proximity to the motor, said second tracking element configured to record a noise signal produced by the motor such that the recorded noise signal can be used to improve the position and/or orientation estimate of the digital tip.

2. The ultrasound catheter of claim 1, wherein the first tracking element is disposed between the motor and the distal tip.

3. The ultrasound catheter of claim 1, wherein the first and/or second tracking elements comprise three generally orthogonal coils.

4. The ultrasound catheter of claim 1, wherein the first and/or second tracking elements comprise a magnetic field sensor.

5. The ultrasound catheter of claim 1, wherein the first tracking element comprises a magnetic field generator.

6. The ultrasound catheter of claim 1, wherein the first tracking element is configured to track the distal tip of the flexible catheter housing with six degrees of freedom.

7. The ultrasound catheter of claim 1, wherein the second tracking element is disposed within the flexible catheter housing between the transducer array and the motor.

8. The surgical navigation system of claim 1, wherein the ultrasound catheter comprises an ICE catheter.

9. A surgical navigation system comprising:
   an ultrasound catheter comprising:
      a flexible catheter housing defining a proximal end and a distal tip;
      a transducer array disposed at least partially within the flexible catheter housing; and
      a motor positioned in the flexible catheter housing and coupled with the transducer array, said motor being configured to rotate the transducer array in order to image a three-dimensional volume;
      a first tracking element adapted to provide an estimate of a position and/or orientation of the distal tip of the flexible catheter housing, said first tracking element disposed immediately adjacent to the distal tip of the flexible catheter housing such that there are no other components disposed between the tracking element and the distal tip so as to track the position and/or orientation of the distal tip within a high degree of precision despite catheter flex;
      a second tracking element disposed within the flexible catheter housing near the motor, said second tracking element being configured to record a noise signal produced by the motor; and
   a tracking system connected to the first tracking element and the second tracking element, said tracking system configured to compensate for the recorded noise signal from the second tracking element in a manner adapted to improve the precision of the position and/or orientation estimate from the first tracking element.

10. The surgical navigation system of claim 9, wherein the first tracking element comprises a magnetic field sensor.

11. The surgical navigation system of claim 9, wherein the first tracking element comprises a magnetic field generator.

12. The surgical navigation system of claim 9, wherein the first tracking element is configured to track the distal tip of the flexible catheter housing with six degrees of freedom.

13. The surgical navigation system of claim 9, wherein, the second tracking element is disposed within the flexible catheter housing between the transducer array and the motor.

14. The surgical navigation system of claim 9, wherein the ultrasound catheter comprises an ICE catheter.

15. The surgical navigation system of claim 9, wherein the first tracking element comprises three generally orthogonal coils.

16. The surgical navigation system of claim 9, further comprising a display adapted to visually convey the estimated position and/or orientation of the distal tip of the flexible catheter housing.

* * * * *